(12) United States Patent
Pazenok et al.

(10) Patent No.: US 10,906,893 B2
(45) Date of Patent: Feb. 2, 2021

(54) METHOD FOR PREPARING METHYL 4-[(4,5-DIHYDRO-3-METHOXY-4-METHYL-5-OXO-1H-1,2,4-TRIAZOL-1-YL) CARBONYL)SULFAMOYL]-5-METHYLTHIOPHENE-3-CARBOXYLATE

(71) Applicants: Bayer CropScience Aktiengesellschaft, Monheim am Rhein (DE); Bayer Aktiengesellschaft, Leverkusen (DE)

(72) Inventors: Sergii Pazenok, Solingen (DE); Christian Funke, Leichlingen (DE); Friedrich August Muehlthau, Kelkheim-Fischbach (DE); Mark James Ford, Wiesbaden-Breckenheim (DE); Arnd Neeff, Burscheid (DE); Klaus-Ulrich Schiffer, Wuppertal (DE)

(73) Assignees: Bayer CropScience Aktiengesellschaft, Monheim am Rhein (DE); Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 16/486,516

(22) PCT Filed: Feb. 15, 2018

(86) PCT No.: PCT/EP2018/053771
§ 371 (c)(1),
(2) Date: Aug. 16, 2019

(87) PCT Pub. No.: WO2018/153767
PCT Pub. Date: Aug. 30, 2018

(65) Prior Publication Data
US 2020/0048234 A1 Feb. 13, 2020

(30) Foreign Application Priority Data

Feb. 23, 2017 (EP) .................................... 17157615

(51) Int. Cl.
*C07D 409/12* (2006.01)

(52) U.S. Cl.
CPC .................................. *C07D 409/12* (2013.01)

(58) Field of Classification Search
None
See application file for complete search history.

(56) References Cited

U.S. PATENT DOCUMENTS

| | | | |
|---|---|---|---|
| 6,964,939 B1 | 11/2005 | Gesing et al. |
| 7,642,221 B2 | 1/2010 | Gesing et al. |
| 7,674,917 B2 | 3/2010 | Geller et al. |
| 7,858,805 B2 | 12/2010 | Gesing et al. |

FOREIGN PATENT DOCUMENTS

| | | |
|---|---|---|
| DE | 19933260 A1 | 1/2001 |
| DE | 10 2004 063192 A1 | 7/2006 |
| WO | 01/05788 A1 | 1/2001 |

OTHER PUBLICATIONS

Rostamnia, Sadegh. Homoleptic chelating N-heterocyclic carbine complexes of palladium immobilized within the pores of SBA-15/IL (NHC—Pd@SBA-15/IL) as heterogeneous catalyst for Hiyana reaction. Journal of Organometallic Chemistry. 791 (2015) 18-23.*
PCT International Search Report for PCT/EP2018/053771, dated May 11, 2018.

* cited by examiner

*Primary Examiner* — Samantha L Shterengarts
(74) *Attorney, Agent, or Firm* — McBee Moore & Vanik IP, LLC

(57) ABSTRACT

The invention relates to a method for preparing methyl 4-[(4,5-dihydro-3-methoxy-4-methyl-5-oxo-1H-1,2,4-triazol-1-yl)carbonyl)sulfamoyl]-5-methylthiophene-3-carboxylate from 4-methoxycarbonyl-2-methylthiophene-3-sulfonyl chloride in the presence of an imidazole base substituted in the 1-position or in the presence of a mixture of bases comprising an imidazole base substituted in the 1-position (N-alkylimidazole).

11 Claims, No Drawings

METHOD FOR PREPARING METHYL 4-[(4,5-DIHYDRO-3-METHOXY-4-METHYL-5-OXO-1H-1,2,4-TRIAZOL-1-YL)CARBONYL)SULFAMOYL]-5-METHYLTHIOPHENE-3-CARBOXYLATE

CROSS-REFERENCE TO RELATED APPLICATIONS

This application is the National Stage entry of International Application No. PCT/EP2018/053771, filed 15 Feb. 2018, which claims priority to European Patent Application No. 17157615.0, filed 23 Feb. 2017.

BACKGROUND

Field

The invention relates to an improved method for preparing methyl 4-[(4,5-dihydro-3-methoxy-4-methyl-5-oxo-1H-1,2,4-triazol-1-yl)carbonyl)sulfamoyl]-5-methylthiophene-3-carboxylate (known under the common name "thiencarbazone-methyl").

Description of Related Art

The herbicidal activity of substituted thien-3-ylsulfonylaminocarbonyltriazolinones is known from the document DE 199 33 260 A1 and from document WO 01/05788 A1, in which the priority of DE 199 33 260 A1 is claimed.

Selected substituted thien-3-ylsulfonylaminocarbonyltriazolinones, such as thiencarbazone-methyl, have particularly good herbicidal activity.

Due to the good activity, improvement of the method for preparing the aforementioned herbicides, also with respect to the environmental compatibility of the preparation, was a constant endeavour of chemical research.

Document DE 19933260 A1 discloses using alternative (c), in addition to four further method alternatives, a method for preparing substituted thien-3-ylsulfonylaminocarbonyltriazolinones by reacting sulfonyl isocyanates with 5-methoxy-4-methyl-2,4-dihydro-3H-1,2,4-triazol-3-one. In the case of these aforementioned method alternatives, the possibility of reacting substituted thiophene-3-sulfonyl chlorides with substituted triazolinones and metal (thio)cyanates, optionally in the presence of a reaction auxiliary and if appropriate in the presence of a diluent, is only outlined by a formula scheme (cf. DE 19933260 A1, page 7), but not verified by a detailed example.

In connection with the method alternatives (a) to (e), optional reaction auxiliaries are disclosed in DE 19933260 A1. For said reactions, these typically refer to acid binders that may be used. The selection mentioned on page 9 of DE 19933260 A1 also comprises potassium tert-butoxide, and basic nitrogen compounds such as amines including tributylamine and pyridines such as 2-methylpyridine, 3-methylpyridine, 5-ethyl-2-methylpyridine, 2,6-dimethylpyridine.

In contrast, imidazoles are not mentioned as reaction auxiliaries in DE 19933260 A1.

Document DE 10 2004 063192 A1 proposes a method starting from sulfonamide and phosgene for preparing the sulfonyl isocyanate using the method alternative disclosed in DE 19933260 A1 (i.e. preparation of thiencarbazone-methyl by reacting sulfonyl isocyanates with 5-methoxy-4-methyl-2,4-dihydro-3H-1,2,4-triazol-3-one).

However, the method disclosed in DE 10 2004 063192 A1, owing to the use of phosgene which is classified as highly toxic, is hazardous and therefore complicated and expensive.

SUMMARY

Against this background, the object of the invention consists of providing an improved method for preparing substituted thien-3-ylsulfonylaminocarbonyltriazolinones, especially thiencarbazone-methyl, i.e. the compound of the formula (I), wherein the improved method is intended to enable the preparation of the target compound thiencarbazone-methyl in high purity and yield.

The object is achieved by the method according to claim 1 for preparing the compound of the formula (I)

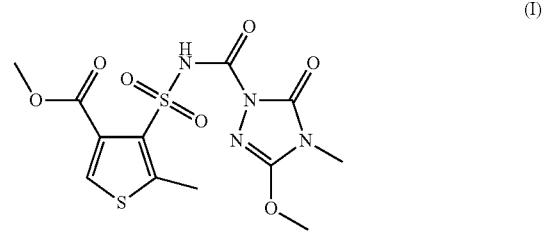

by reacting the compound of the formula (II)

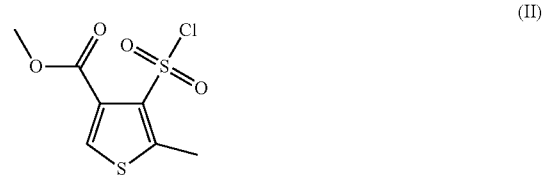

with a metal cyanate of the formula (III)

MeOCN      (III), where Me is Li, Na, K or Cs
with the compound of the formula (IV)

wherein the reaction is carried out in the presence of an imidazole of the formula (V)

DETAILED DESCRIPTION OF A PREFERRED EMBODIMENT where the radical R1 is an unsubstituted $(C_1-C_{12})$-alkyl or an unsubstituted benzyl.

It has been found, surprisingly, in the context of the method according to the invention, that the use of alkyl-substituted imidazoles, especially N-alkylimidazoles, enables the preparation of substituted thien-3-ylsulfonylaminocarbonyltriazolinones, especially the preparation of methyl 4-[(4,5-dihydro-3-methoxy-4-methyl-5-oxo-1H-1,2,4-triazol-1-yl)carbonyl)sulfamoyl]-5-methylthiophene-3-carboxylate(thiencarbazone-methyl), in a particularly high purity and yield.

The invention is therefore based on the finding that the compound of the formula (I), thiencarbazone-methyl, under certain conditions, namely in the presence of an imidazole base substituted in the 1-position or in the presence of a mixture of bases comprising an imidazole base substituted in the 1-position (N-alkylimidazole), can be prepared directly from 4-methoxycarbonyl-2-methylthiophene-3-sulfonyl chloride (compound of the formula (II)) with high purity and yield.

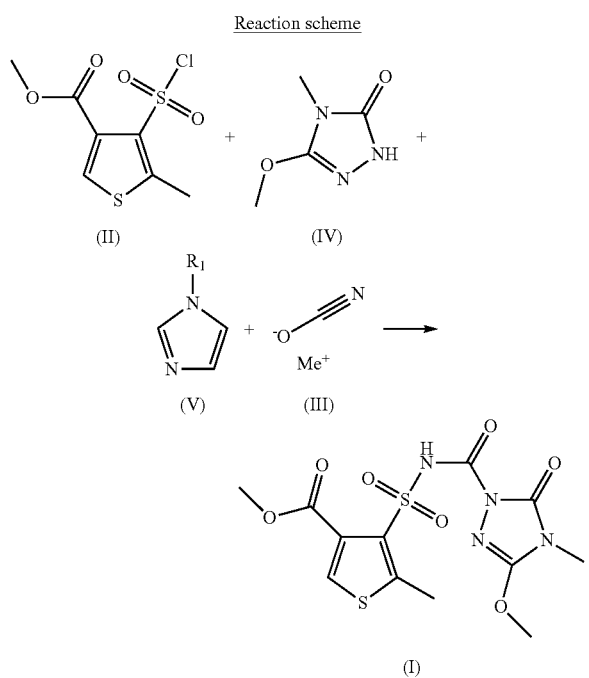

Reaction scheme

The reaction scheme above shows that, when carrying out the reaction as a one-pot synthesis at the start of the reaction, a 4-component system is present.

In the case of a two-stage reaction regime, the reactant 5-methoxy-4-methyl-2,4-dihydro-3H-1,2,4-triazol-3-one of the formula (IV) is only added to the mixture after formation of the sulfonyl isocyanate from compounds of the formulae (II) and (III) in the presence of an N-alkylimidazole of the formula (V).

The synthesis of the reactants, i.e. the synthesis of the compounds of the formula (II) and (IV) in the reaction scheme above, is disclosed in DE 19933260 A1. The compounds of the formula (III) and (V) are commercially available.

It is assumed that the imidazoles substituted by an alkyl radical in the 1-position (N-alkylimidazoles) act particularly well as activators (=activating agents) in the formation of the sulfonyl isocyanate and/or stabilizers in the formation of the sulfonyl isocyanate.

However, the core of the present invention relates to the surprising finding that the metal cyanate reacts selectively with the sulfonyl group of the respective thiophene compound (with the methyl 4-(chlorosulfonyl)-5-methylthiophene-3-carboxylate of the formula (II) in the above scheme) in the presence of an N-alkylimidazole of the formula (V) to give a sulfonyl isocyanate, and that from this the substituted thien-3-ylsulfonylaminocarbonyltriazolinone (the target compound thiencarbazone-methyl (I) in the above reaction scheme) is subsequently formed.

The unexpected selectivity of the reaction presented in the scheme consists of the fact that the triazolinone (IV) only reacts after formation of the sulfonyl isocyanate further with the same to give thiencarbazone-methyl.

In addition, with regard to the use of a metal cyanate in a chemical reaction, it is of quite general concern that metal cyanates are strong bases (sodium cyanate (NaOCN), for example, has a pH of 10). At the same time, metal cyanates act as 0-nucleophiles.

In the presence of an N-alkylimidazole, especially in the presence of N-methylimidazole, the 0-nucleophilicity of the metal cyanate used in accordance with the invention surprisingly but particularly does not affect the course of the present reaction, i.e. the yield and selectivity thereof.

This does not apply to the use of other basic nitrogen compounds such as pyridines, picolines or 4-(dimethylamino)pyridine (DMAP), which can be considered as classical activators of carbonyl halides for example. The same applies to the use of inorganic bases such as $K_2CO_3$ or potassium tert-butoxide (KOtBu) which have also proven to be unsuitable.

For instance, it has been verified by example that the yield of thiencarbazone-methyl when using the method according to the invention is unexpectedly high in comparison to carrying out the reaction using other alternative basic nitrogen compounds.

The method according to the invention is preferably carried out in the presence of an imidazole of the formula (V), where the radical $R_1$ is an unsubstituted $(C_1-C_6)$-alkyl, or an unsubstituted benzyl. Carrying out the method in the presence of an imidazole of the formula (V), where the radical R1 is a substituted $(C_1-C_6)$-alkyl or a substituted benzyl is not preferred but also lies within the scope of the invention.

The method according to the invention is particularly preferably carried out in the presence of an imidazole of the formula (V), where the radical R1 is an unsubstituted $(C_1-C_4)$-alkyl. Very particular preference is given to unbranched $(C_1-C_4)$-alkyl, i.e. methyl, ethyl, n-propyl or n-butyl as R1.

The method according to the invention is most preferably carried out in the presence of N-methylimidazole (NMI), i.e. when the radical $R_1$ in formula (V) is methyl.

To prepare the compound of the formula (I) by the method according to the invention, the reagents are preferably used in equimolar amount or in excess.

In general, for each mole of sulfonyl chloride, i.e. the compound of the formula (II), 1 to 2.5 mol, preferably 1 to 2 mol, particularly preferably 1 to 1.8 mol of the metal cyanate of the formula MeOCN (III) are used. However, the use of larger excesses of the compound of the formula (III) also lies within the scope of the invention.

In a preferred embodiment, Me in compounds of the formula MeOCN (III) is Na or K. The most preferred metal cyanate in the method according to the invention is NaOCN.

Furthermore, generally for each mole of sulfonyl chloride, likewise 1 to 2 mol, preferably 1 to 1.5 mol, particularly preferably 1 to 1.1 mol of (5-methoxy-4-methyl-2,4-dihydro-3H-1,2,4-triazol-3-one), i.e. of the compound of the formula (IV) are used.

However, the use of larger excesses of the compound of the formula (IV) also lies within the scope of the invention.

The method is carried out in an organic solvent, wherein non-polar and polar solvents are suitable.

Suitable non-polar solvents are toluene, chlorobenzene, xylene, methyl tert-butyl ether, methyl isopropyl ether, ethyl acetate, isopropyl acetate and butyl acetate.

Polar solvents are particularly preferably selected from the group consisting of acetonitrile, butyronitrile, tetrahydrofuran (THF), methyl-THF, dimethoxyethane, sulfolane, dimethylformamide and dimethylacetamide.

Most preferred as solvent are acetonitrile and THF.

Mixtures of different solvents may also be used.

The reaction of the reactants is preferably conducted in a temperature range of 20° to 110° over a period (reaction time, reaction period) of 3 hours to 24 hours.

Very particular preference is given to the reaction of the reactants in a temperature range of 30° to 90°. The reaction of the reactants is most preferably conducted in a temperature range of 50° to 80°.

A further aspect of the invention relates to the use of an imidazole of the formula (V)

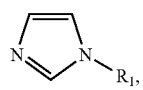

(V)

where the radical $R_1$ is an unsubstituted $(C_1-C_{12})$-alkyl or an unsubstituted benzyl, for preparing the compound of the formula (I)

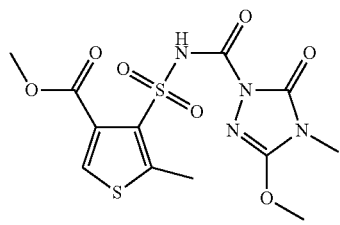

(I)

Preference is given to the use of an imidazole of the formula (V), where $R_1$ is an unsubstituted $(C_1-C_4)$-alkyl.

Particular preference is given to the use of an imidazole of the formula (V), where $R_1$ is an unbranched and unsubstituted $(C_1-C_4)$-alkyl, i.e. methyl, ethyl, n-propyl or n-butyl.

Most preferred is the use of an imidazole of the formula (V), where $R_1$ is methyl.

EXAMPLES

The preparation method according to the invention may be carried out as a one-pot method or as a two-stage reaction.

In the one-pot method, all chemicals are mixed in an organic solvent and then heated with stirring. In order to better control the exothermicity of the reaction, it is also advisable to initially charge the reagents of the formula (III), (IV) and (V) in acetonitrile for example, in order to then slowly meter in the sulfonyl chloride of the formula (II) as a solution at the reaction temperature.

During the reaction the active ingredient or salt thereof precipitates from the reaction mixture and can then be simply filtered off.

It is particularly advantageous at the end of the reaction to add to the mixture an inorganic base such as LiOH, $K_2CO_3$, $NaHCO_3$, NaOH, $Na_2CO_3$, $CaCO_3$ or KOH in order to isolate the active ingredient as an insoluble Li, Na, K or Ca salt. The use of $NaHCO_3$ is preferred. In this way it is possible to isolate the active ingredient in very high purity.

The amount of base to be used depends on how much metal cyanate is used when carrying out the reaction. When using only 1 equivalent (eq) of NaOCN, then 1 eq. of base is correspondingly required in order to convert the active ingredient completely to the salt (Example 1). For example, if 2 eq of metal cyanate, e.g. 2 eq of NaOCN, is used to carry out the reaction, no additional base is required (cf. Example 3).

By treating the salt with an acid (e.g. HCl, $H_2SO_4$), the active ingredient is released and isolated after filtration.

It is also possible to react firstly the compound of the formula (II) with MeOCN in the presence of the compound of the formula (V) in order to produce the sulfonyl isocyanate of the formula (VI). Then, in a second step, the sulfonyl isocyanate, optionally without prior isolation, is reacted with 5-methoxy-4-methyl-2,4-dihydro-3H-1,2,4-triazol-3-one of the formula (IV).

The analysis, identification and determination of the content of sulfonyl isocyanate after step 1 is based on derivatization with methanol to give the corresponding carbamate of the formula (VII).

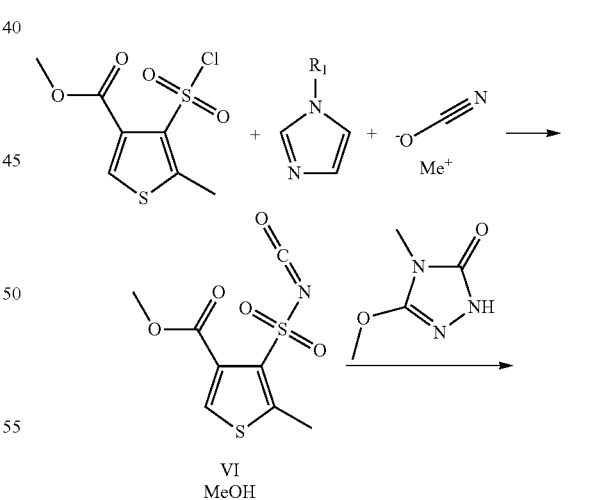

VI
MeOH

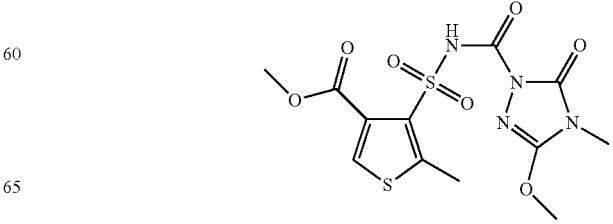

-continued

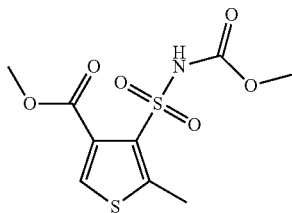

VII

If necessary, the isocyanate can be isolated and purified by vacuum distillation.

TABLE 1

Tabular comparison of the yields by LC analysis using various reaction auxiliaries for preparing methyl 4-[(4,5-dihydro-3-methoxy-4-methyl-5-oxo-1H-1,2,4-triazol-1-yl)carbonyl)-sulfamoyl]-5-methylthiophene-3-carboxylate (thiencarbazone-methyl), in acetonitrile, NaOCN 2 eq.

| Comparison No. | Amount of activator/mol. eq. | Time (hr)/T ° C. | Target product LC, area % |
|---|---|---|---|
| 1 | 2-Methylpyridine/1 | 12/80 | 26 |
| 2 | 3-Methylpyridine/1 | 12/80 | 36 |
| 3 | 3-Methylpyridine/0.1 | 12/80 | 25 |
| 4 | 2-methyl-5-ethylpyridine/1 | 12/80 | 27 |
| 5 | 2-Methyl-5-ethylpyridine/5 | 12/80 | 29 |
| 6 | p-Dimethylaminopyridine/0.5 | 12.80 | 34 |
| 7 | 2,6-dimethylpyridine/1 | 12 (80) | 37 |
| 8 | Tributylamine/1 | 12 (60) | 5 |
| 9 | KOtBu/1 | 12 (80) | 0 |
| 10 | N-Butylimidazole/1 | 12 (80) | 84 |
| 11 | N-Methylimidazole/1 | 12 (80) | 92 |
| 12 | N-Methylimidazole/0.8 | 12 (80) | 91 |

The table above confirms that the yield of thiencarbazone-methyl when using the method according to the invention and using N-butylimidazole and N-methylimidazole is unexpectedly high in comparison to other nitrogen bases. In contrast, in the case of comparative use of the nitrogen base tributylamine, the target product thiencarbazone-methyl is detectable in a low % range by liquid chromatography (LC). When using the acid binder potassium tert-butoxide (KOtBu), product detection is not even possible.

SYNTHESIS EXAMPLES

Example 1

Methyl 4-[(4,5-dihydro-3-methoxy-4-methyl-5-oxo-1H-1,2,4-triazol-1-yl)carbonyl)sulfamoyl]-5-methyl-thiophene-3-carboxylate (one-pot method)

25.4 g of methyl 4-(chlorosulfonyl)-5-methylthiophene-3-carboxylate, 6.5 g of NaOCN, 12.9 g of N-methylimidazole and 12.9 g of 5-methoxy-4-methyl-2,4-dihydro-3H-1,2,4-triazol-3-one are initially charged in 200 ml of acetonitrile and heated to 70° C. The mixture was heated at this temperature with stirring for 12 hr and cooled to 20° C.

To the mixture were added 8.5 g of NaHCO₃ and the suspension was further stirred at 20° C. for 3 hr. The precipitate was filtered off, washed with 50 ml of 10% HCl and 100 ml of water and dried at 50° C. This gave 31.6 g of methyl 4-[(4,5-dihydro-3-methoxy-4-methyl-5-oxo-1H-1,2,4-triazol-1-yl)carbonyl)sulfamoyl]-5-methylthiophene-3-carboxylate, 80% of theory with a melting point of 201° C., and a purity of 99%.

Example 2

Methyl 4-[(4,5-dihydro-3-methoxy-4-methyl-5-oxo-1H-1,2,4-triazole-1-yl)carbonyl)sulfamoyl]-5-methylthiophene-3-carboxylate (one-pot method)

25.4 g. of methyl-4-(chlorosulfonyl)-5-methylthiophen-3-carboxylate, 11.7 g NaOCN, 8.2 g N-methylimidazol and 12.9 g 5-methoxy-4-methyl-2,4-dihydro-3H-1,2,4-triazol-3-one are initially charged in 220 ml of acetonitrile and heated to 70° C. The mixture was heated at this temperature with stirring for 18 hr and cooled to 20° C. To the mixture were added 1.7 g NaHCO₃ and the suspension was further stirred at 20° C. for 2 hr. The mixture was heated to 60° C., the precipitate was filtered off and washed with 50 ml with 50 ml acetonitrile. After that the precipitate was washed with 70 ml of 20% H₂SO₄, 100 ml of hot (70° C.) water and 50 ml of acetone and dried at 50° C. This gave 31.4 g of methyl 4-[(4,5-dihydro-3-methoxy-4-methyl-5-oxo-1H-1,2,4-triazole-1-yl)carbonyl)sulfamoyl]-5-methylthiophene-3-carboxylate, 79% of theory with a purity of 98%.

Example 3

Methyl 4-[(4,5-dihydro-3-methoxy-4-methyl-5-oxo-1H-1,2,4-triazol-1-yl)carbonyl)sulfamoyl]-5-methyl-thiophene-3-carboxylate (one-pot method)

25.4 g of methyl 4-(chlorosulfonyl)-5-methylthiophene-3-carboxylate, 13 g of NaOCN, 12.9 g of N-methylimidazole and 12.9 g of 5-methoxy-4-methyl-2,4-dihydro-3H-1,2,4-triazol-3-one are initially charged in 200 ml of acetonitrile and heated to 70° C. The mixture was heated at this temperature with stirring for 12 hr and cooled to 20° C.

The precipitate was filtered off, washed with 50 ml of 10% HCl and 100 ml of water and dried at 50° C. This gave 33.6 g of methyl 4-[(4,5-dihydro-3-methoxy-4-methyl-5-oxo-1H-1,2,4-triazol-1-yl)carbonyl)sulfamoyl]-5-methyl-thiophene-3-carboxylate, 84.4% of theory with a purity of 98%.

Example 4

Methyl 4-[(4,5-dihydro-3-methoxy-4-methyl-5-oxo-1H-1,2,4-triazol-1-yl)carbonyl)sulfamoyl]-5-methyl-thiophene-3-carboxylate (two-stage method)

25.4 g of methyl 4-(chlorosulfonyl)-5-methylthiophene-3-carboxylate, 6.5 g of NaOCN, 12.9 g of N-methylimidazole were initially charged in 150 ml of acetonitrile and the mixture was heated at 50° C. for 4 hr. The suspension was filtered through a glass frit under argon and 12.5 g of 5-methoxy-4-methyl-2,4-dihydro-3H-1,2,4-triazol-3-one were added to the filtrate. The mixture was then heated at 70° C. for 8 hr and cooled to 20° C.

To the mixture were added 8 g of NaHCO₃ and 1 ml of water and the suspension was stirred for a further 3 hr. The precipitate was filtered off, washed with 50 ml of 10% HCl and 100 ml of water and dried at 50° C. This gave 29.6 g of methyl 4-[(4,5-dihydro-3-methoxy-4-methyl-5-oxo-1H-1,2,4-triazol-1-yl)carbonyl)sulfamoyl]-5-methylthiophene-3-carboxylate, 75.6% of theory with a melting point of 201° C., and a purity of >99%.

Example 5

Methyl 4-[(4,5-dihydro-3-methoxy-4-methyl-5-oxo-1H-1,2,4-triazole-1-yl)carbonyl)sulfamoyl]-5-methylthiophene-3-carboxylate (two-stage method)

25.4 g of methyl-4-(chlorosulfonyl)-5-methylthiophen-3-carboxylate, 11.7 g NaOCN, 12.3 g N-methylimidazole were initially charged in 150 ml of acetonitrile and the mixture was heated at 50° C. for 4 hr. The suspension was filtered through a glass frit under argon and 12.5 g of 5-methoxy-4-methyl-2,4-dihydro-3H-1,2,4-triazol-3-one were added to the filtrate. After that the mixture was heated at 70° C. for 12 hr and and cooled to 20° C.

To the mixture were added 1.7 g of NaHCO$_3$ and 1 ml of water and the suspension was stirred for a further 3 hr. The precipitate was filtered off, washed with 50 ml of 10% HCl and 100 ml of water and dried at 50° C. This gave 30.5 g of methyl 4-[(4,5-dihydro-3-methoxy-4-methyl-5-oxo-1H-1,2,4-triazole-1-yl)carbonyl)sulfamoyl]-5-methylthiophene-3-carboxylate, 77% of theory and a purity of 98%.

Example 6

Methyl 4-(methoxycarbonylsulfamoyl)-5-methylthiophene-3-carboxylate 25.4 g of methyl 4-(chlorosulfonyl)-5-methylthiophene-3-carboxylate, 6.5 g of NaOCN, 12.9 g of N-methylimidazole were initially charged in 150 ml of acetonitrile and the mixture was heated at 50° C. for 4 hr. The suspension was filtered through a glass frit under argon and 30 ml of methanol were added. After 1 hr, the solution was fully concentrated and the precipitate washed with water and dried. This gave 24 g of methyl 4-(methoxycarbonylsulfamoyl)-5-methylthiophene-3-carboxylate H NMR: (d$^6$ DMSO) 2.72 (s), 3.62 (s), 3.79 (s), 8.01 (s), 12.01 (s) ppm).

The invention claimed is:

1. A method for preparing a compound of formula (I)

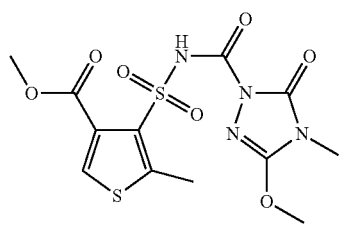

(I)

by reacting the compound of formula (II)

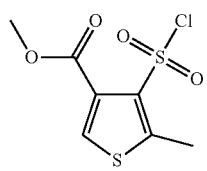

(II)

with a metal cyanate of formula (III)

MeOCN    (III), where Me is Li, Na, K or Cs
and
with a compound of formula (IV)

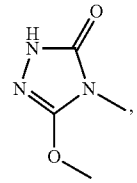

(IV)

wherein the reaction is carried out in the presence of an imidazole of formula (V)

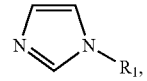

(V)

where the radical $R_1$ is an unsubstituted $(C_1-C_{12})$-alkyl or an unsubstituted benzyl.

2. The method for preparing a compound of formula (I) according to claim 1, wherein $R_1$ is an unsubstituted $(C_1-C_6)$-alkyl or an unsubstituted benzyl.

3. The method for preparing a compound of formula (I) according to claim 2, wherein $R_1$ is an unsubstituted $(C_1-C_4)$-alkyl.

4. The method for preparing a compound of formula (I) according to claim 3, wherein $R_1$ is methyl, ethyl, n-propyl or n-butyl.

5. The method for preparing a compound of formula (I) according to claim 4, wherein $R_1$ is methyl.

6. The method for preparing a compound of formula (I) according to claim 1, wherein Me in a compound of formula MeOCN (III) is Na or K.

7. The method for preparing a compound of formula (I) according to claim 1, wherein the reaction is carried out in a polar solvent selected from the group consisting of acetonitrile, butyronitrile, tetrahydrofuran (THF), methyl-THF, dimethoxyethane, sulfolane, dimethylformamide and dimethylacetamide.

8. The method for preparing a compound of formula (I) according to claim 1, wherein the reaction is carried out in a solvent mixture comprising acetonitrile and THF.

9. The method for preparing a compound of formula (I) according to claim 1, wherein the reaction is conducted
in a temperature range of 20° to 110° and
in a reaction time of 3 hours to 24 hours.

10. The method for preparing a compound of formula (I) according to claim 9, wherein the reaction is conducted in a temperature range of 30° to 90°.

11. The method for preparing a compound of formula (I) according to claim 10, wherein the reaction is conducted in a temperature range of 50° to 80°.

* * * * *